United States Patent [19]

Bohen et al.

[11] Patent Number: 5,208,366

[45] Date of Patent: May 4, 1993

[54] HIGH YIELD METHOD FOR PREPARATION OF DIALKYL ESTERS OF POLYHALOAROMATIC ACIDS

[75] Inventors: Joseph M. Bohen, King of Prussia; Anthony J. Mancuso, Trappe, both of Pa.

[73] Assignee: Elf Atochem North America, Inc., Philadelphia, Pa.

[21] Appl. No.: 738,992

[22] Filed: Aug. 19, 1991

Related U.S. Application Data

[63] Continuation of Ser. No. 244,421, Sep. 16, 1988, Pat. No. 5,049,697, which is a continuation-in-part of Ser. No. 99,361, Sep. 21, 1987, abandoned.

[51] Int. Cl.⁵ .............................................. C07C 67/08
[52] U.S. Cl. ....................................... 560/83; 560/99; 560/103; 560/106; 560/112; 562/480; 562/493
[58] Field of Search .................. 560/83, 99, 103, 106, 560/112

[56] References Cited

U.S. PATENT DOCUMENTS

| | | | |
|---|---|---|---|
| 3,162,616 | 12/1964 | Dombrow et al. | 560/99 X |
| 3,749,134 | 7/1973 | Slingluff et al. | 560/83 X |
| 3,929,866 | 12/1975 | Baldino et al. | 560/83 |
| 3,933,721 | 1/1976 | Wilson | 560/83 X |
| 3,957,835 | 5/1976 | Chien et al. | 260/349 |
| 4,007,218 | 2/1977 | Ghanayem et al. | 560/204 |
| 4,098,704 | 7/1978 | Sandler | 252/8.6 |
| 4,298,517 | 11/1981 | Sandler | 524/288 |
| 4,375,551 | 3/1983 | Finley | 560/83 |
| 4,405,761 | 9/1983 | Rodgers et al. | 560/83 X |
| 4,564,697 | 1/1986 | Sutker | 560/83 |
| 4,675,434 | 6/1987 | Uhm et al. | 560/99 |
| 4,754,053 | 6/1988 | Mamuzic et al. | 560/83 X |
| 4,764,550 | 8/1988 | Lovenguth | 524/217 |

FOREIGN PATENT DOCUMENTS 47-47981 12/1972 Japan.
50-05701 3/1975 Japan.
810381 3/1959 United Kingdom.

OTHER PUBLICATIONS

Chemical Abstracts, vol. 70, No. 20: 88598e, (1969).
Chemical Abstracts, vol. 90, No. 16: 122565s, (1979).
Chemical Abstracts, vol. 104, No. 22: 187714s, (1986).
Pape, et al., Journal of Cellular Plastics, Nov., 1968, pp. 438–442.
Nordlander et al., Journal of the American Chemical Society, vol. 69, Nov. 1947, pp. 2679–2682.

Primary Examiner—José G. Dees
Assistant Examiner—Vera C. Clarke
Attorney, Agent, or Firm—Panitch Schwarze Jacobs & Nadel

[57] ABSTRACT

An improved process is provided for the preparation of esters of polyhalophthalic acids, polyhalobenzoic acids, and polyhalophthalic anhydride useful as flame retardants for thermoplastic and thermosetting resins, which comprises the reaction of the above acids or anhydride with alcohols in the presence of certain metal and metallorganic compounds as catalysts. Also provided are certain esters per se.

6 Claims, No Drawings

HIGH YIELD METHOD FOR PREPARATION OF DIALKYL ESTERS OF POLYHALOAROMATIC ACIDS

This application is a continuation-in-part of Ser. No. 244,421, filed Sep. 16, 1988, now allowed as U.S. Pat. No. 5,049,697, which in turn is a continuation-in-part of Ser. No. 099,361 filed Sep. 21, 1987, now abandoned.

BACKGROUND OF THE INVENTION

1. Field of the Invention

This invention relates to methods for preparing polyhaloaromatic carboxylic esters, some of these esters per se, and the use of some esters as flame retardants and/or processing aids.

2. Statement of Related Art

A number of processes have been developed for the preparation of diesters of the phthalic acids and phthalic anhydride from alcohols using traditional strong acid esterification catalysts, such as sulfuric acid, p-toluenesulfonic acid, hydrochloric acid, etc. However, when the aromatic rings are polyhalogenated, complete esterification becomes slow and difficult, resulting in low yields and poor product quality which make these processes commercially unattractive.

Pape, Sanger and Nametz (J. of Cellular Plastics, November, 1968, p. 438) discloses that diesters of tetrabromophthalic anhydride can be prepared only with great difficulty and in low yields. Pape, et al., used epoxides to convert the free-carboxyl group of the intermediate monoester to a hydroxy-substituted ester.

Spatz, et al., (I & EC Product Res. and Dev., 8, 391, 1969) used phosphoric acid as a catalyst to prepare the di-2-ethylhexyl ester of tetrabromophthalic acid with only 60% yield. Substantial decarboxylation of the intermediate half-ester was also observed.

Baldino and Feltzin in U.S. Pat. No. 3,929,866 reported the preparation of diesters from alcohols containing at least 3 hydroxyl groups; however, no products were isolated and no yield details are given.

Finley in U.S. Pat. No. 4,375,551 prepared allylic esters of tetrabromophthalic anhydride by first preparing the half-ester and then converting the half-ester to the sodium salt which was then treated with allyl chloride in the presence of phase transfer catalysts.

The use of metallic salts of tetrachlorophthalic anhydride to prepare diesters has been documented by several workers. Nordlander and Cass (J.A. Chem. Soc. 69, 2679 (1947)) disclose that diesters of tetrachlorophthalic acid have been prepared by reacting a metallic salt of the acid with an alkyl halide or sulfate, or by reacting tetrachlorophthalyl chloride with a sodium alcoholate. Nordlander et al. also disclose the direct esterification of tetrachlorophthalic anhydride using acid-catalyzed, non-catalyzed high temperature, and base-catalyzed high temperature reactions. The acid-catalyzed reaction yields ranged from poor to fair (10 to 70%).

Lawlor (I. & EC, 39, 1419 (1947)) reported low yields of diesters could be obtained from either the sodium or silver salts of the intermediate half-ester of tetrachlorophthalic anhydride or from the acid chloride, tetrachlorophthaloyl chloride.

Nomura, et al., in Japan published Patent Application 75-05701 discloses the use of alkyl titanates together with alkali or alkaline earth metal salts (hydroxide, carbonate, bicarbonate, or salt of organic acid) for the esterification of tetrabromophthalic acid or anhydride with alcohols to produce the corresponding diesters. These alkali or alkaline earth materials are an essential part of the Nomura, et al., catalyst system, whether added together with the alkyl titanate or at different times during the process in order to obtain products having low acid numbers.

SUMMARY OF THE INVENTION

The method of the invention is for preparing esters of polyhaloaromatic carboxylic acids and anhydrides of the general formula I.

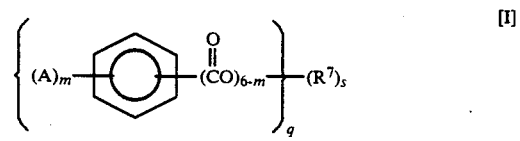

wherein:
(a) the aromatic rings can have all possible isomeric arrangements;
(b) A is Br or Cl;
(c) m is 3, 4, or 5;
(d) q is an integer of 1 to 6;
(e) $R^7$ is:
 (i) a substituted or unsubstituted, $C_{1-30}$ (preferably $C_{1-22}$, most preferably $C_{1-18}$) alkyl or an aryl having up to 30 (preferably 22, most preferably 18) carbon atoms, and with a valence (v) which is an integer of 1 to 4;

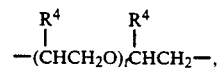

where:
$R^3$ is H or a substituted or unsubstituted $C_{1-30}$ (preferably $C_{1-22}$, most preferably $C_{1-18}$) alkyl, or an aryl having up to 30 (preferably 22, most preferably 18) carbon atoms,
$R^4$ is, independently, H or $CH_3$,
p is an integer of 1 to 50, and
t is an integer of 1 to 49; or

where $R^5$ is a substituted or unsubstituted, $C_{1-30}$ (preferably $C_{1-22}$, most preferably $C_{1-18}$) alkyl or an aryl having up to 30 (preferably 22, most preferably 18) carbon atoms; and

q, m, and v being as above defined.
The method comprises reacting
(i) at least one polyhaloaromatic carboxylic acid or anhydride of the general formulas

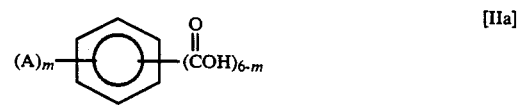

or

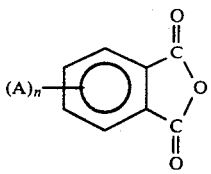
[IIb]

wherein A is Br or Cl, m is 3, 4 or 5, and n is 3 or 4;

(ii) at least a stoichiometric quantity of at least one alcohol or polyol of the general formula $$R^7(OH)_v$$

wherein $R^7$ and v are as defined for general formula I; and (iii) a catalytically effective amount of at least one metal or organometallic compound which is:

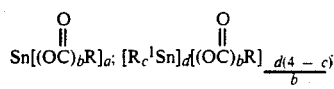

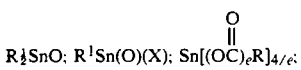

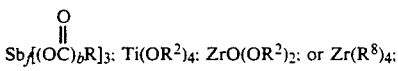

wherein:
(a) R, independently, is: H, a substituted or unsubstituted $C_{1-30}$ (preferably $C_{1-22}$, most preferably $C_{1-18}$) alkyl; a substituted or unsubstituted $C_{2-22}$ alkenyl; a $C_{1-18}$ alkylene; or not present;
(b) $R^1$ is a $C_{1-8}$ alkyl or cyclo-$C_{1-8}$-alkyl;
(c) X is OH,

$O_{0.5}$, or Cl;
(d) $R^2$, independently, is a substituted or unsubstituted $C_{1-30}$ (preferably $C_{1-22}$, most preferably $C_{1-18}$)alkyl; or a substituted or unsubstituted $C_{2-22}$ alkylene;
(e) $R^8$, independently, is $OR^2$ or the residue of a 1,3 dicarbonyl compound of the formula:

where $R^6$, independently, is H, $OR^2$, or a substituted or unsubstituted $C_{1-30}$ (preferably $C_{1-22}$, most preferably $C_{1-18}$)alkyl;
(f) a and b are 1 or 2 with the proviso that a and b cannot be the same;
(g) c and d are 1 or 2 with the proviso that d can be 2 only when c is 1 and b is 2;
(h) b is 2 if R is not present;
(i) e is 1 or 2; and
(j) f is 1 or 2 with the proviso that b equals f.

The invention includes the use of the various reactants and catalyst systems specified herein and, where novel, the various esters per se and/or prepared by the method of the invention.

Another embodiment of this invention is that novel esters of difficult to esterify polyhaloaromatic carboxylic acids and anhydrides are provided, which esters are useful as flame retardants and processing aids. These novel esters have the general formula II:

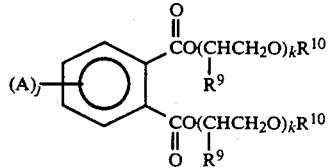

wherein:
(a) A is as defined for general formula I;
(b) j is 3 or 4;
(c) k is an integer of 1 to 50;
(d) $R^9$ is H or $CH_3$; and
(e) $R^{10}$ is H, a $C_{1-30}$ alkyl, or a substituted or unsubstituted aryl having up to 30 carbon atoms.

The reaction conditions should be such that a complete esterification of the acid or anhydride is achieved, producing a full (as contrasted with half- or semi-)ester. To achieve this, the mol ratio of reactants (polyhaloaromatic carboxylic acid or anhydride):(alcohol or polyol) is 1:1–10.0, preferably 1:1–5.0; and the mol ratio (polyhalocarboxylic acid or anhydride):(metallic or organometallic catalyst) is 1:0.0005–0.1, preferably 1:0.001–0.05.

The reaction is completed by the removal of the water by-product of the esterification. To accomplish this the reactants preferably are heated to reflux, with continual water by-product removal until no further water is produced. A similar result could be achieved by reacting at lower temperatures, with water by-product removal in any known manner. The temperature will vary with the reactants and the pressure and, while reflux temperatures are generally satisfactory, it may be advantageous with some reactants to use a partial vacuum and thus lower the reflux temperature. The excess alcohol or polyol usually will act as a solvent for the reaction. Where this is inadequate, or where the alcohol or polyol is water-miscible, an organic solvent which forms an azeotrope with water and which is inert to the reaction may be added. Such a solvent may also act favorably to adjust the effective reaction temperature. Useful solvents include, but are not limited to, toluene, xylene, heptane, tetrahydronaphthalene, and the like. It also is advantageous to conduct the reaction under agitation, since this not only promotes contact of the reactants with each other, but also frees water by-product from the reaction mass, facilitating its removal. Generally, if the water by-product is not removed, the esterification will not go to completion. It may be noted that auxiliary co-catalysts such as the alkaline salts described by Nomura, et al., supra, are neither required nor desirable in this invention.

DETAILED DECRIPTION OF THE INVENTION

Other than in the operating examples, or where otherwise indicated, all numbers expressing quantities of ingredients or reaction conditions used herein are to be understood as modified in all instances by the term "about".

It has been found that certain metal and organometallic compounds are excellent catalysts for the difficult to achieve complete esterification of polyhaloaromatic carboxylic acids and anhydrides. These catalysts permit the esterification to proceed in high yields with high purity, thus making this process commercially attractive.

The inventive process for preparing esters of polyhaloaromatic carboxylic acids and anhydrides comprises reacting at least one polyhaloaromatic carboxylic acid or anhydride with at least one alcohol or polyol in the presence of at least one metal or organometallic catalyst compound.

The process described above may be represented in general terms by one of the following reaction sequences (1 and 2).

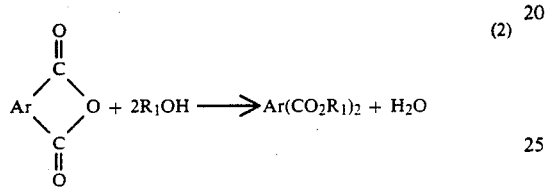

where Ar is a polyhaloaromatic group and R$_1$OH is an alcohol or polyol.

The time of the reaction is indefinite, since it is allowed to proceed until the reactant present in a lesser amount is substantially reacted. typically, in laboratory preparations, the time was 2 to 22 hours, although a time as long as 73 hours was efficacious in one instance.

Examples of representative metal and organometallic catalysts are as follows:

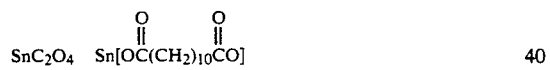

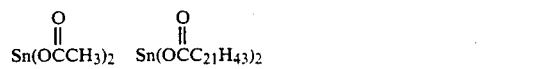

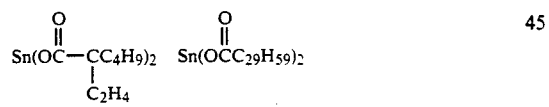

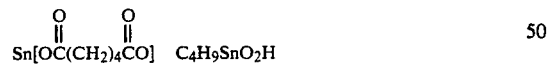

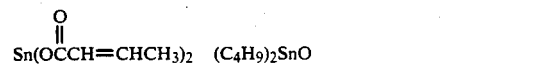

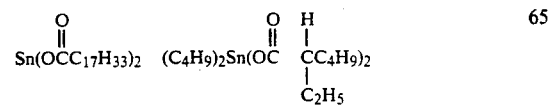

-continued

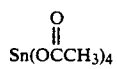

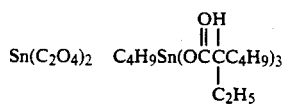

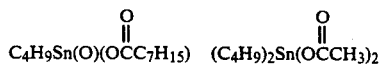

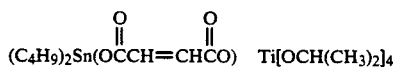

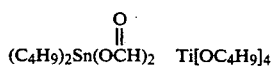

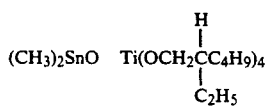

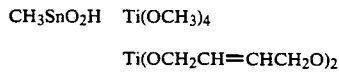

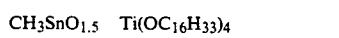

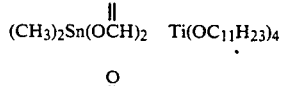

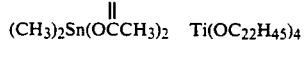

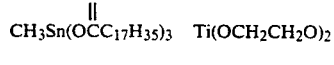

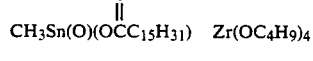

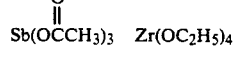

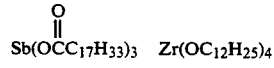

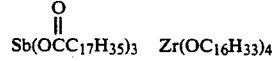

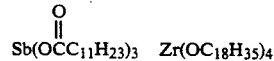

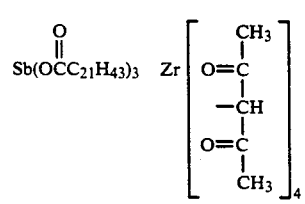

-continued $$Sb(O\overset{O}{\overset{\|}{C}}C_3H_7)_3$$

$$Sb(O\overset{O}{\overset{\|}{C}}C_8H_{17})_3 \quad Zr\begin{bmatrix} O=C-C_4H_9 \\ -CH \\ O=C \\ | \\ O \\ | \\ C_2H_5 \end{bmatrix}_4$$

$$Sb(O\overset{O}{\overset{\|}{C}}\overset{OH}{\overset{|}{C}}C_4H_9)_3$$
$$\quad\quad\quad\quad |$$
$$\quad\quad\quad\quad C_2H_5$$

$$Sb_2(O\overset{O}{\overset{\|}{C}}CH=CH\overset{O}{\overset{\|}{C}}O)_3 \quad ZrO(OC_4H_9)_2$$

$$Sb_2[O\overset{O}{\overset{\|}{C}}(CH_2)_8\overset{O}{\overset{\|}{C}}O]_3 \quad Zr[OCH(CH_3)_2]_4$$

Preferred catalysts are the following:

$$SnC_2O_4 \quad Sb(O\overset{O}{\overset{\|}{C}}C_{17}H_{33})_3$$

$$Sn(O\overset{O}{\overset{\|}{C}}CC_4H_9)_2 \quad Sb(O\overset{O}{\overset{\|}{C}}CH_3)_3$$
$$\quad | \quad\quad\quad$$
$$\quad C_2H_5$$

$$(C_4H_9)_2SnO \quad Sb(O\overset{O}{\overset{\|}{C}}C_{17}H_{35})_3$$

$$C_4H_9SnO_2H \quad Sb(O\overset{O}{\overset{\|}{C}}C_{15}H_{31})_3$$

$$\quad\quad\quad\quad\quad\quad CH_3$$
$$\quad\quad\quad\quad\quad\quad |$$
$$C_4H_9SnO_{1.5} \quad Ti(O\overset{}{C}H)_4$$
$$\quad\quad\quad\quad\quad\quad |$$
$$\quad\quad\quad\quad\quad\quad CH_3$$

$$C_4H_9Sn(O)(Cl) \quad Ti(OC_4H_9)_4$$

$$(C_4H_9)_2Sn(O\overset{O}{\overset{\|}{C}}C_{11}H_{23})_2 \quad Zr\begin{bmatrix} CH_3 \\ O=C \\ -CH \\ O=C \\ | \\ CH_3 \end{bmatrix}_4$$

$$Sn(O\overset{O}{\overset{\|}{C}}CHC_4H_9)_2 \quad Zr\begin{bmatrix} CH_3 \\ O=C \\ -CH \\ O=C-OC_2H_5 \end{bmatrix}_4$$
$$\quad | \quad\quad\quad$$
$$\quad C_2H_5$$

The amount of catalyst employed in the preparation of the polyhaloaromatic carboxylic esters of this invention alternatively may be given as 0.0001 to 5.0 (preferably 0.01 to 2.0) parts per part of polyhaloaromatic carboxylic acid or anhydride, where the alcohol or polyol is present in greater than a stoichiometric amount to the acid or anhydride.

The aromatic acids and anhydrides that are operable in this invention have the formulas:

$$(A)_m-\text{C}_6\text{H}-(\overset{O}{\overset{\|}{C}}OH)_{6-m} \text{ or } (A)_n-\text{C}_6\text{H}-\begin{matrix}\overset{O}{\overset{\|}{C}}\\ O \\ \overset{O}{\overset{\|}{C}}\end{matrix}$$

wherein:
m is an integer of 3 to 5,
n is an integer of 3 to 4, and
A is Cl or Br.

Examples of representative polyhaloaromatic carboxylic acids and anhydrides are as follows:

[Structural formulas of various brominated and chlorinated aromatic acids and anhydrides shown]

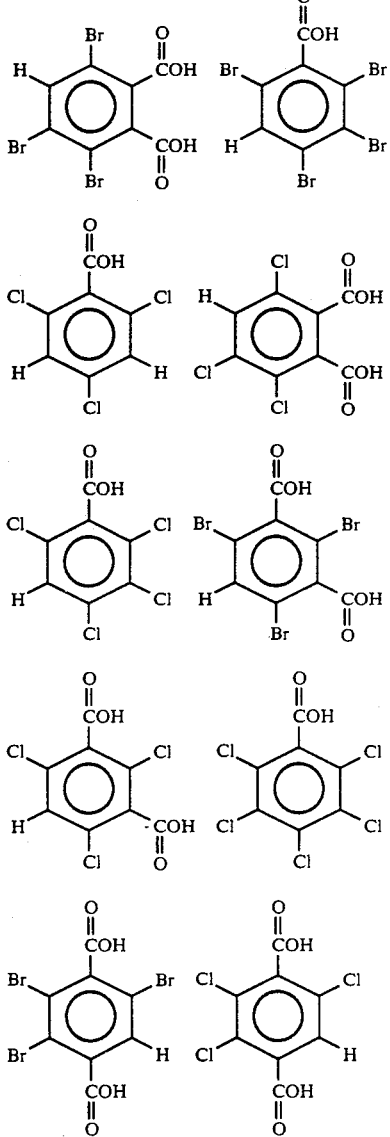

The alcohols that can be used in this invention have the formula:

R⁷(OH)ᵥ wherein $R^7$ and v are as defined for general formula I. Examples of representative alcohols and polyols are as follows:

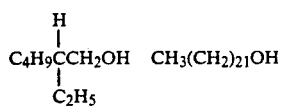

CH₃OCH₂CH₂OH   CH₃(CH₂)₂₉OH

CH₃O(CH₂CH₂O)₂H   HOCH₂CH₂CH₂OH

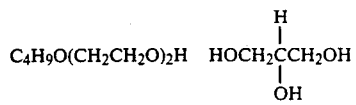

C₄H₉OCH₂CH₂OH   C(CH₂OH)₄

C₈H₁₇OH   C₂H₅C(CH₂OH)₃

HOCH₂CH₂OH   CH₃C(CH₂OH)₃

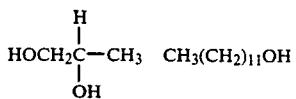

CH₃(CH₂)₁₇OH   (CH₃)₂ĊCH₂OH

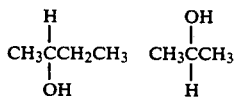

CH₃(OCH₂CH₂)₇OH   CH₃CO(CH₂CH₂O)₃H

CH₃(OCH₂CH₂)₁₀₋₃₀OH   HO(CH—CH₂O)₂₀H
                                           |
                                           CH₃

HO(CH₂CH₂O)₄H

HO(CH₂CH₂O)₁₂H

CH₃COCH₂CH₂OH   CH₃OH

HO(CH₂CH₂O)₂₀₋₅₀H   CH₃CH₂OH

HO(CHCH₂O)₆H   CH₃(CH₂)₄OH
    |
    CH₃

Examples of representative esters that can be prepared in high yields by using the catalysts of this invention are as follows (where A is Br or Cl):

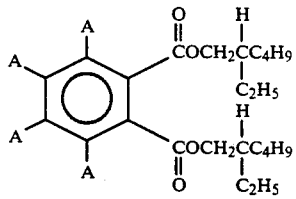

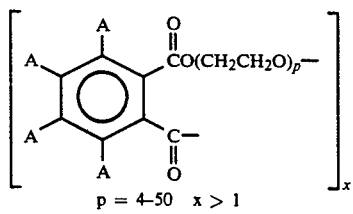

p = 4-50   x > 1

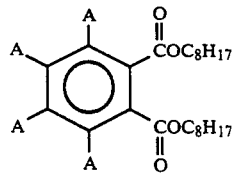

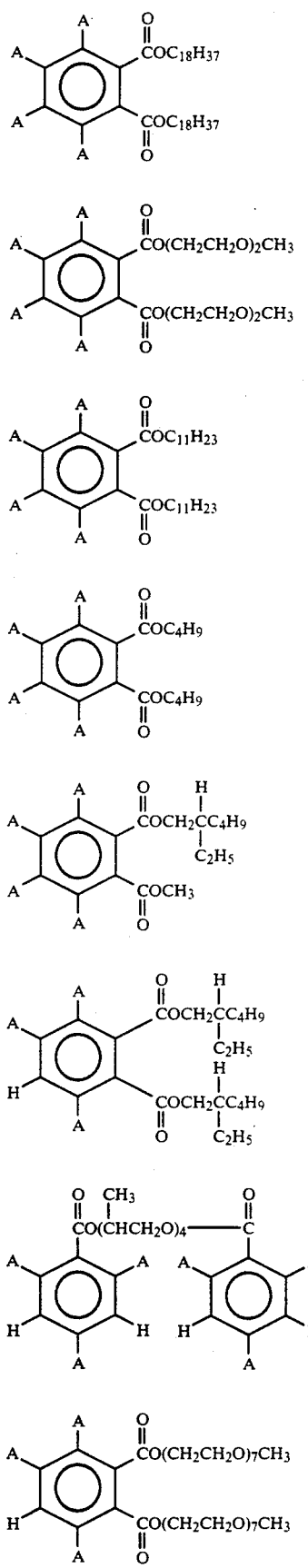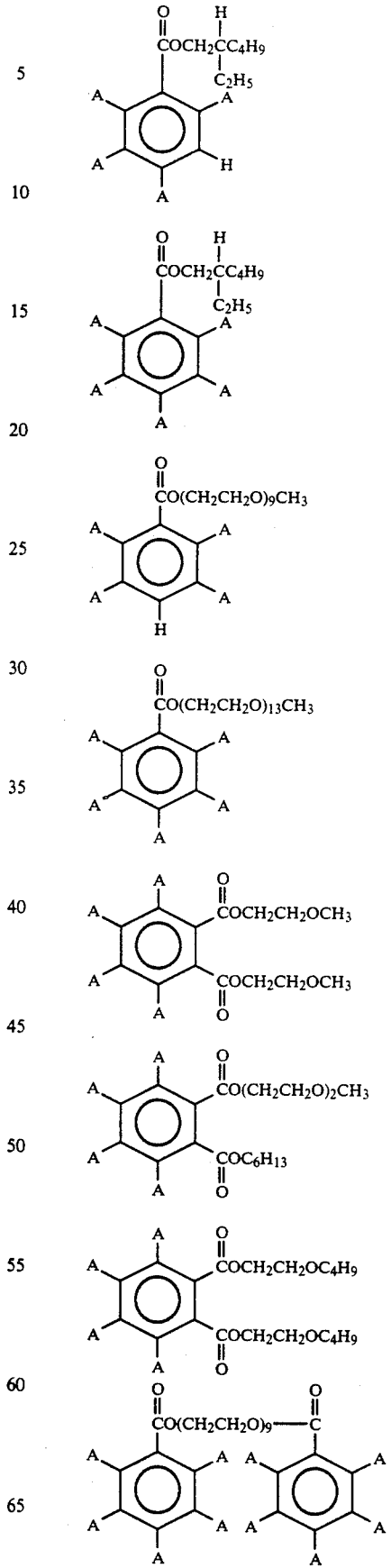

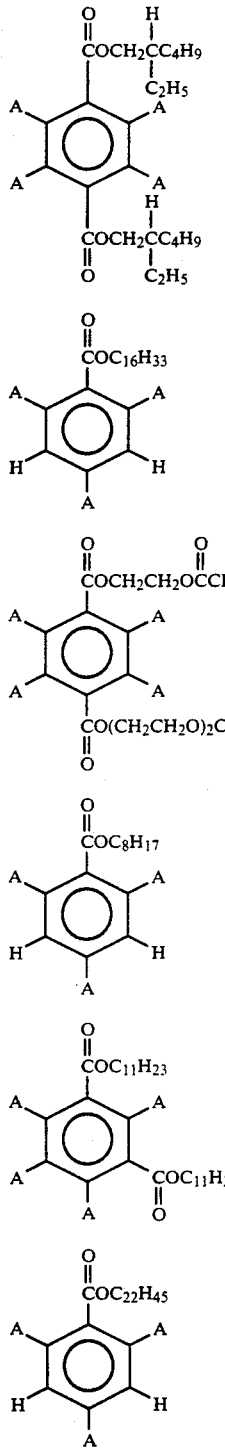

The diesters of this invention are useful as flame retardants and/or flameproofing agents when incorporated in and/or applied to a variety of inflammable thermoplastic and thermosetting polymers.

Such polymers comprise hydrocarbon polymers including saturated, unsaturated, linear, atactic, crystalline or non-linear amorphous polymers, copolymers, terpolymers, and the like, such as polyethylene, polypropylene, poly(4-methyl pentene-1), polybutene-1, polystyrene, styrene-butadiene rubber, butyl rubber, natural rubber, polyisobutylene, ethylene-propylene- copolymer, cis-1-4-polyisoprene, ethlene-propylene-dicyclopentadiene terpolymer, and blends of these polymers with each other.

Also useful in this invention are nonhydrocarbon polymers such as the unsaturated polyesters; drying and non-drying alkyd resins; linear-saturated polyesters such as poly(ethylene terephthalate), poly(1,4-cyclohexanedimethylene terephthalate) and poly(1,4-butylene terephthalate); polyurethanes; poly(alkylene oxides) such as poly(ethylene oxide) and poly(propylene oxide), and the like; poly(arylene oxides) such as poly(phenylene oxide); polyamides such as nylon; poly(vinyl alkyl ethers) such as poly(vinyl methyl ether), ethylene-vinyl acetate copolymers; poly(ethyl acrylate), poly(ethyl methacrylate); polysulfones; epoxy resins; butadiene-terpolymers; plasticized poly(vinyl chloride); and the like.

The following examples are illustrative of the invention.

EXAMPLE 1

Into a one liter three-necked flask, equipped with an overhead mechanical stirrer, a Dean Stark trap, a water condenser with a nitrogen inlet and a thermometer were charged 231.86 gm (0.50 mol) of tetrabromophthalic anhydride, 390.7 gm (3.0 mols) of 2-ethyl-1-hexanol, and 2.32 gm of stannous oxalate. The flask and contents were stirred and heated to reflux (195° C.) and 9 ml of water (100% of theory) were obtained in 22 hours. The contents were cooled to room temperature, filtered to remove the catalyst, and the excess of alcohol was removed by vacuum distillation to give 350 gm of a light yellow oil. The yield was 97%. Calculated % Br 45.3, Found % Br, 44.9. Analytical data was consistent with the assigned structure. High pressure liquid chromatography (HPLC) of the product showed it to be 96.2% pure with only a minor amount of by-product (3.3%) due to decarboxylation of the intermediate half-ester which contrasts with the results obtained by Spatz, et al., (I & EC Products Res. and Des., 8 391 (1969).

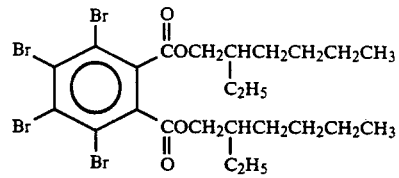

EXAMPLE 2

Following the procedure outlined in Example 1 using 6955.8 gm (15.0 mols) of tetrabromophthalic anhydride 11.72 kg (90.15 mols) 2-ethyl-1-hexanol, and 69.55 gm of stannous oxalate, resulted in 10.5 kg (99% yield) of di-2-ethylhexyl tetrabromophthalate. Calculated % Br. 45.3, Found % Br 43.5. Analytical data was consistent with the assigned structure. High pressure liquid chromatography (HPLC) of the product showed it to be 97.1% pure with only a minor amount of by-product (2.8%) due to decarboxylation of the intermediate half-ester.

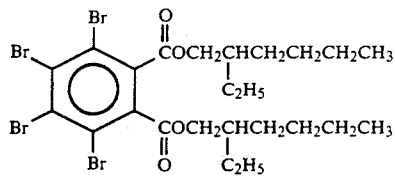

EXAMPLE 3

Into a two liter three-necked flask, equipped with an overhead mechanical stirrer, Dean Stark trap, a water condenser with a nitrogen inlet tube and a thermometer were charged 463.72 gm (1.0 mol) of tetrabromophthalic anhydride, 442.78 gm (3.4 mols) of 2-ethyl-1-hexanol and 6.50 gm (0.022 mols) of titanium tetraisopropoxide. The flask and contents were heated to reflux (198° C.) and 23.2 gm of a water phase were collected in 5 hours. (Note: The aqueous phase contained isopropyl alcohol which was derived from the catalyst. If all of the isopropyl groups were converted to isopropyl alcohol, this would amount to 5.3 gm which plus the expected water (18 gm) totals 23.3 gm). The excess 2-ethyl-1-hexanol was removed by vacuum distillation to give 703.7 gm of a light yellow oil. The yield was 99.6%. Calculated % Br, 45.3, Found % Br, 45.0. Analytical data was consistent with the assigned structure. High pressure liquid chromatography showed it to be 98.5% pure with only a minor amount of by-product (1.3%) due to decarboxylation of the intermediate half-ester.

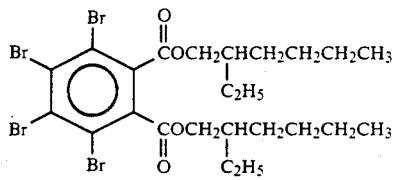

EXAMPLE 4

This compound can be prepared following the procedure outlined in Example 1 except using 1-dodecanol instead of 2-ethyl-1-hexanol.

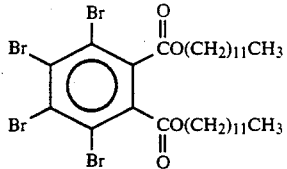

EXAMPLE 5

Into a two liter three-necked flash, equipped with an overhead mechanical stirrer, Dean Stark trap, a water condenser with a nitrogen inlet tube and a thermometer, were charged 463.7 gm (1.0 mol) of tetrabromophthalic anhydride, 442.7 gm (3.4 mols) of 1-octanol and 4.6 gm of stannous oxalate. The flask and contents were heated to reflux (210° C.) and 22.5 gm of a water phase were collected in 7 hours. The excess 1-octanol was removed on a rotary evaporator to give 696 gm of a dark oil. The yield was 98.6%.

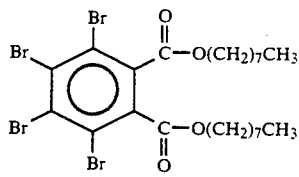

EXAMPLE 6

This compound can be prepared following the procedure in Example 1 except using isononyl alcohol instead of 2-ethyl-1-hexanol.

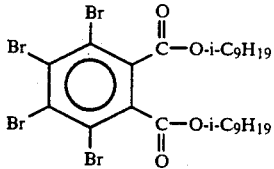

EXAMPLE 7a

Tetrabromophthalic anhydride, 231.9 gm (0.5 mol), 2-(2-methoxyethoxy)-ethanol, 360.5 gm (3.0 mols), stannous oxalate, 2.32 gm, and xylene, 200 ml, were refluxed (temp. 160° C.) for 18 hours during which time, theory water was collected. The xylene and excess 2-(2-methoxyethoxy)-ethanol were distilled under reduced pressure to give 332 gm of crude product as a wet white solid. 256 gm of this material were redissolved in toluene (1000 ml) and extracted with 3 times 200 ml of a 7.5% potassium bicarbonate solution followed by one extraction with 200 ml of water. The organic phase was dried overnight with anhydrous magnesium sulfate overnight. After removing the magnesium sulfate by filtration, toluene was removed by distillation to give a yellow liquid product. Calculated % Br, 46.6. Found % Br, 45.7. Analytical data was consistent with the assigned structure.

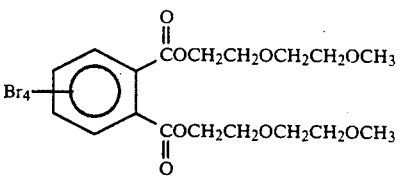

EXAMPLE 7b

The yield in Example 7a was considered too low, and so it was partially repeated, using slightly different parameters but with a longer reflux time.

Tetrabromophthalic anhydride, 231.9 gm (0.5 mol), 2-(2-methoxyethoxy)-ethanol, 360.5 gm (3.0 mols), stannous oxalate, 2.32 gm, 0.2 gm KOAc and xylene, 100 ml were refluxed (temp. 171° C.) for 73 hours during which time, theory water was collected. 150 ml of toluene was added to the reaction mixture and it was then washed with a 15% NaCl solution. The washed organic was extracted with 2 times 200 ml of a 7.5% potassium bicarbonate solution followed by two extractions with a 15% NaCl solution. The organic phase was dried overnight with anhydrous magnesium sulfate. After removing the magnesium sulfate by filtration, toluene and xylene were removed by distillation to give 246.6 gm of yellow liquid product in 72% yield. Calculated % Br, 46.6. Found % Br, 46.9. Analytical data was consistent with the assigned structure for Example 7a.

EXAMPLE 8

This compound was prepared by the procedure outlined in Example 7a except using 2-(2-ethoxyethoxy)-ethanol in place of 2-(2-methoxyethoxy)-ethanol. The yield was acceptable.

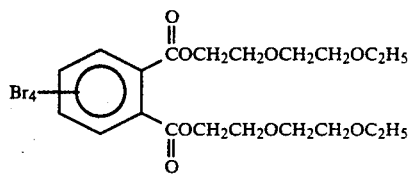

EXAMPLE 9

This compound can be prepared by the procedure outlined in Example 3 except using isodecyl alcohol in place of 2-ethyl-1-hexanol.

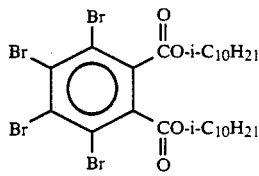

EXAMPLE 10

This compound can be prepared following the procedure outlined in Example 1 except using n-butyl alcohol instead of 2-ethyl-1-hexanol and butylstannoic acid as the catalyst instead of stannous oxalate.

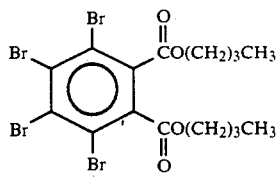

EXAMPLE 11

This compound can be prepared following the procedure outlined in Example 1 except using 1-octadecanol instead of 2-ethyl-1-hexanol.

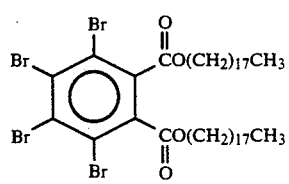

EXAMPLE 12

Into a one liter three-necked flash, equipped with an overhead mechanical stirrer, Dean Stark trap, a water condenser with a nitrogen inlet tube and a thermometer, were charged 285.9 gm (1.0 mol) of tetrachlorophthalic anhydride, 442.7 gm (3.4 mol) of 2-ethyl-1-hexanol and 6.5 gm of titanium tetrakisisopropoxide. The flask and contents were heated to reflux (200° C.) and 23 gm of a water phase were collected in 2 hours. The excess 2-ethyl-1-hexanol was removed on a rotary evaporator to give 528 gm of an oil. The yield was 100%.

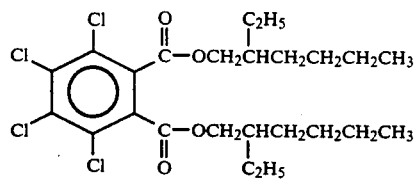

EXAMPLE 13

This compound can be prepared following the procedure outlined in Example 3 except using cyclohexanol instead of 2-ethyl-1-hexanol.

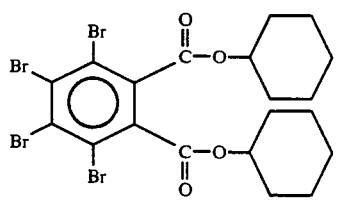

EXAMPLE 14

This compound can be prepared following the procedure outlined in Example 1 except using tribromophthalic anhydride instead of tetrabromophthalic anhydride.

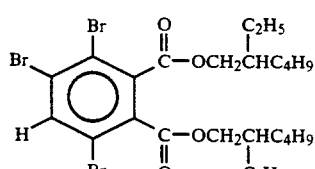

EXAMPLE 15

This compound can be prepared following the procedure outlined in Example 1 except using 1,12-dodecanediol instead of 2-ethyl-1-hexanol and dibutyltin dilaurate instead of stannous oxalate.

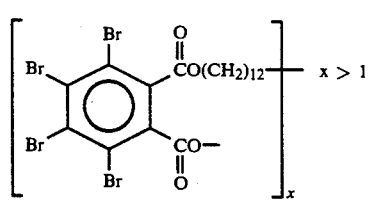

EXAMPLE 16

This compound can be prepared following the procedure outlined in Example 1 except using zirconium tetraacetylacetonate as catalyst instead of stannous oxalate.

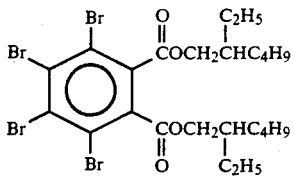

EXAMPLE 17

Into a two liter three-necked flask, equipped with an overhead mechanical stirrer, Dean Stark trap, a water condenser with a nitrogen inlet tube and a thermometer, were charged 927.5 gm (2 mol) of tetrabromphthalic anhydride, 780 gm (6 mols) of 2-ethyl-1-hexanol and 9.27 gm of titanium tetrabutoxide. The flask and contents were heated to reflux 185° C. at 560 mm pressure and 73 gm of a water phase were collected in 10 hours. The excess 2-ethyl-1-hexanol was removed on a rotary evaporator to give 1350 gm of oil. The yield was 96%. Analytical data was consistent with the assigned structure.

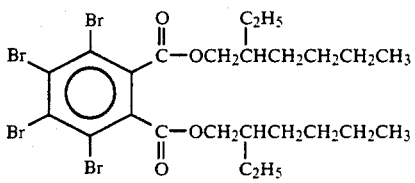

EXAMPLE 18

This compound can be prepared following the procedure outlined in Example 2 except using 1-octanol instead of 2-ethyl-1-hexanol and using stannous oleate as catalyst instead of stannous oxalate.

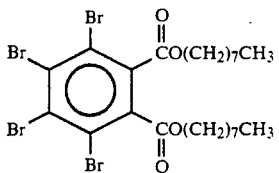

EXAMPLE 19

This compound can be prepared following the procedure outlined in Example 2 except using zirconium tetrapropoxide as a catalyst instead of stannous oxalate.

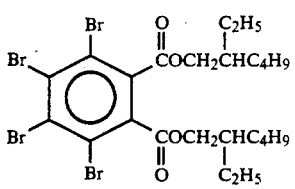

EXAMPLE 20

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromphthalic anhydride, 177 gm (1.36 mols) of 2-ethyl-1-hexanol and 1.85 gm of antimony tris(2-ethyl-hexanoate). The flask and contents were heated to reflux (192° C.) and 7.8 gm of a water phase were collected in 7 hours. The excess 2-ethyl-1-hexanol was removed on a rotary evaporator to give 253.7 gm of an oil. The yield was 90%. Analytical data was consistent with the assigned structure.

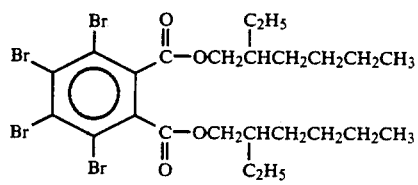

EXAMPLE 21

This compound can be prepared following the procedure outlined in Example 2 except using 1-octanol instead of 2-ethyl-1-hexanol and using titanium tetrabutoxide as a catalyst instead of stannous oxalate.

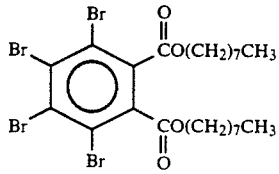

EXAMPLE 22

This compound can be prepared following the procedure outlined in Example 3 except using 2,3,5,6,-tetrabromophthalic acid instead of tetrabromophthalic anhydride.

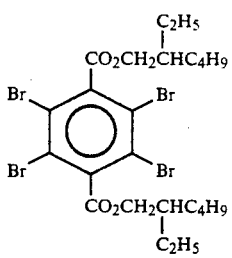

EXAMPLE 23

This compound can be prepared following the procedure outlined in Example 3 except using 2,4,5,6,-tetrabromoisophthalic acid instead of tetrabromophthalic anhydride.

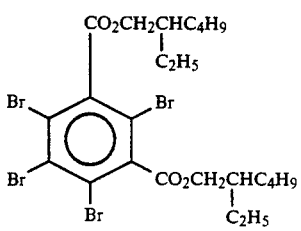

EXAMPLE 24

This compound can be prepared following the procedure outlined in Example 3 except replacing three-fourths of the 2-ethyl-1-hexanol by an equimolar quantity of 1-butanol and refluxing the 2-ethyl-1-hexanol for 2–3 hours prior to the addition of the remaining alcohol.

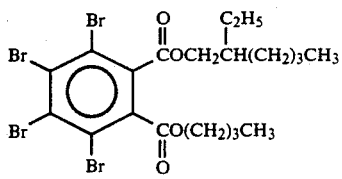

EXAMPLE 25

This compound can be prepared following the procedure outlined in Example 24 except using 1-hexanol instead of 2-ethyl-1-hexanol and using 2-ethoxyethoxyethanol instead of 1-butanol.

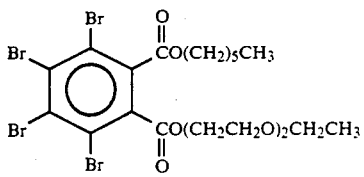

EXAMPLE 26

This compound can be prepared following the procedure outlined in Example 24 except using cyclohexanol instead of 1-butanol.

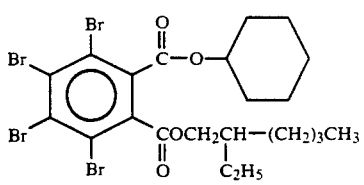

EXAMPLE 27

This compound can be prepared following the procedure outlined in Example 24 except using 1-decanol instead of 2-ethyl-1-hexanol. In addition tetrachlorophthalic anhydride should be used in place of tetrabromophthalic anhydride and butylstannoic acid should be used as the catalyst instead of stannous oxalate.

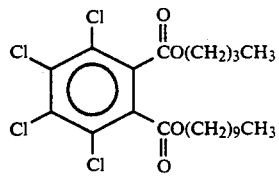

EXAMPLE 28

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of antimony oxalate. The flask and contents were heated to reflux (195° C.) and 7.7 gm of water phase were collected in 6 hours. The excess 2-ethyl-1-hexanol was removed on a rotary evaporator to give 242.8 gm of an oil. The yield was 86%. Analytical data was consistent with the assigned structure.

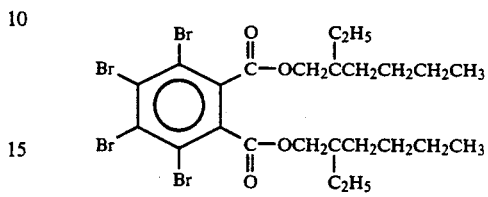

EXAMPLE 29

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of tin (IV) oxide. The flask and contents were heated to reflux (190° C.) and 7.7 gm of a water phase were collected in 10 hours. The excess 2-ethyl-1-hexanol was removed on a rotary evaporator to give 225.6 gm of an oil. The yield was 80%. Analytical data was consistent with the assigned structure.

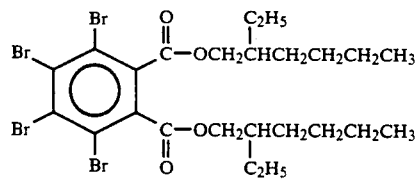

EXAMPLE 30

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of dibutyl tin oxide. The flask and contents were heated to reflux (195° C.) and 8.0 gm of a water phase were collected in 10 hours. The excess 2-ethyl-1-hexanol was removed on a rotary evaporator to give 234 gm of an oil. The yield was 83%. Analytical data was consistent with the assigned structure.

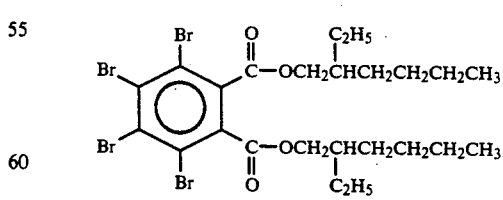

EXAMPLE 31

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.88 gm of butylstannoic anhydride. The flask and contents were heated to reflux (198° C.) and 7.7 gm of a water phase were collected in 4.5 hours. The excess 2-ethyl-1-hexanol was removed on a rotary evaporator to give 273 gm of an oil. The yield was 96.8%. Analytical data was consistent with the assigned structure.

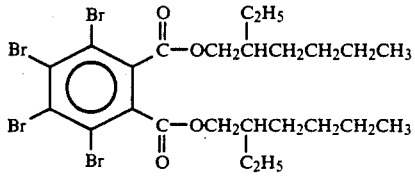

EXAMPLE 32

Into a 500 ml three-necked flask, equipped with an overhead mechanical stirrer, Dean stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.86 gm of dibutyl tin diacetate. The flask and contents were heated to reflux (192° C.) and 8.4 gm of a water phase were collected in 12 hours. The excess 2-ethyl-1-hexanol was removed on a rotary evaporator to give 228 gm of an oil. The yield was 81%. Analytical data was consistent with the assigned structure.

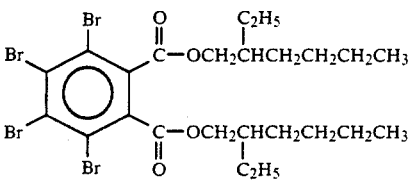

EXAMPLE 33

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of tin (II) 2-ethyl-1-hexanoate. The flask and contents were heated to reflux (198° C.) and 6.0 gm of a water phase were collected in 8.5 hours. The excess 2-ethyl-1-hexanol was removed on a rotary evaporator to give 260 gm of an oil. The yield was 92.1%. Analytical data was consistent with the assigned structure.

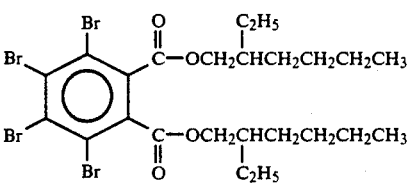

EXAMPLE 34

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of dibutyltin dilaurate. The flask and contents were heated to reflux (194° C.) and 8.0 gm of a water phase were collected in 7 hours. The excess 2-ethyl-1-hexanol was removed on a rotary evaporator to give 260.3 gm of an oil. The yield was 92.3%. Analytical data was consistent with the assigned structure.

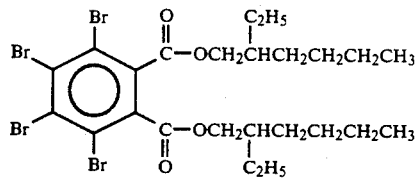

EXAMPLE 35

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of titanium bis(ethyl acetoacetato) diisopropoxy. The flask and contents were heated to reflux (194° C.) and the water phase were collected in 3 hours. The excess 2-ethyl-1-hexanol was removed on a rotary evaporator to give 248 gm of an oil. The yield was 88%. Analytical data was consistent with the assigned structure.

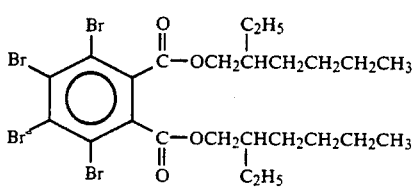

EXAMPLE 36

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of titanium tetrakis(2-ethyl-1-hexanol). The flask and contents were heated to reflux (195° C.) and 7.9 gm of a water phase were collected in 6 hours. The excess 2-ethyl-1-hexanol was removed on a rotary evaporator to give 245 gm of an oil. The yield was 90%. Analytical data was consistent with the assigned structure.

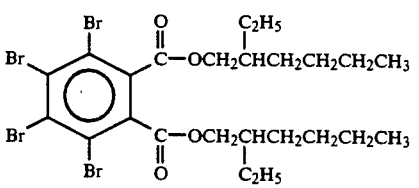

EXAMPLE 37

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 3.7 gm of a 50% solution of zirconium pentyloxide in 1-pentanol. The flask and contents were heated to reflux (172° C.) and 8.2 gm of a water phase were collected in 4½ hours. The excess 2-ethyl-1-hexanol was removed on a rotary evaporator to give 214 gm of an oil. The yield was 76%. Analytical data was consistent with the assigned structure.

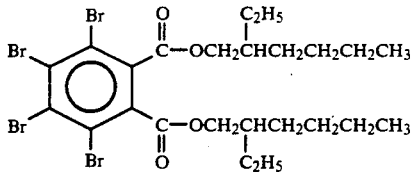

EXAMPLE 38

Into a 500 ml three-necked flask, equipped with an overhead mechanical stirrer, Dean Stark trap, a water condenser with a nitrogen inlet tube and a thermometer, were charged 185.5 gm (0.4 mol) of tetrabromophthalic anhydride, 177 gm (1.36 mols) of 2-ethyl-1-hexanol and 1.85 gm of zirconium oxalate. the flask and contents were heated to reflux (180° C.) and 7.5 gm of a water phase were collected in 6 hours. The excess 2-ethyl-1-hexanol was removed on a rotary evaporator to give 253.8 gm of an oil. The yield was 90%. Analytical data was consistent with the assigned structure.

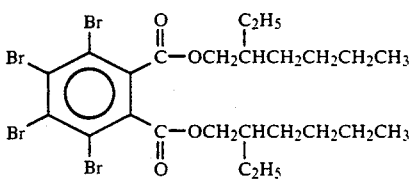

EXAMPLE 39

Into a one liter three-necked flask, equipped with an overhead mechanical stirrer, Dean Stark trap, a water condenser with a nitrogen inlet tube and a thermometer, were charged 285.9 gm (1.0 mol) of tetrachlorophthalic anhydride, 442.7 gm (3.4 mols) of 1-octanol and 3.0 gm of butylstannoic anhydride. The flask and contents were heated to reflux (216° C.) and 18.8 gm of a water phase were collected in 2 hours. The excess 1-octanol was removed on a rotary evaporator to give 522 gm of an oil. The yield was 99%.

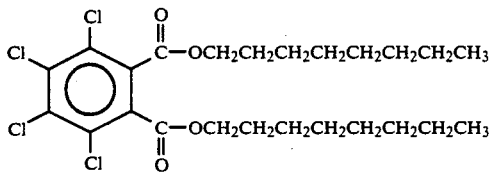

EXAMPLE 40

Into a one liter three-necked flask, equipped with an overhead mechanical stirrer, Dean Stark trap, a water condenser with a nitrogen inlet tube and a thermometer, were charged 285.9 gm (1.0 mol) of tetrachlorophthalic anhydride, 442.7 gm (3.4 mols) of 2-ethyl-1-hexanol and 3.3 gm of stannous oxalate. The flask and contents were heated to reflux (200° C.) and 19.8 gm of a water phase were collected in 3 hours. The excess 2-ethyl-1-hexanol was removed on a rotary evaporator to give 508 gm of a light colored oil. The yield was 96.2%.

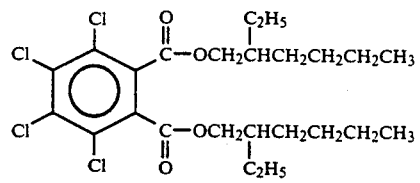

EXAMPLE 41

Into a one liter three-necked flask, equipped with an overhead mechanical stirrer, Dean Stark trap, a water condenser with a nitrogen inlet tube and a thermometer, were charged 285.9 gm (1.0 mol) of tetrachlorophthalic anhydride, 442.7 gm (3.4 mols) of 2-ethyl-1-hexanol and 3.3 gm butylstannoic anhydride. The flask and contents were heated to reflux (200° C.) and 20 gm of a water phase were collected in 2 hours. The excess 2-ethyl-1-hexanol was removed on a rotary evaporator to give 527 gm of a light colored oil. The yield was 100%.

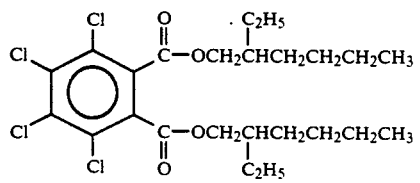

EXAMPLE 42

Into a two liter three-necked flask, equipped with an overhead mechanical stirrer, Dean Stark trap, a water condenser with a nitrogen inlet tube and a thermometer, were charged 572 gm (2.0 mols) of tetrachlorophthalic anhydride, 885 gm (6.8 mols) of 2-ethyl-1-hexanol and 6.6 gm of stannous oxalate. The flask and contents were heated to reflux (196° C.) and 40.0 gm of a water phase were collected in 6 hours. The excess 2-ethyl-1-hexanol was removed on a rotary evaporator to give 952 gm of a light colored oil. The yield was 90%.

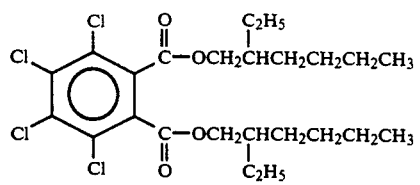

EXAMPLE 43

Into a two liter three-necked flask, equipped with an overhead mechanical stirrer, Dean Stark trap, a water condenser with a nitrogen inlet tube and a thermometer, were charged 285.9 gm (1.0 mol) of tetrachlorophthalic anhydride, 347.5 gm (3.4 mols) of 2-ethyl-1-butanol, 400 gm of tetrahydronapthalene (organic solvent) and 3.3 gm of stannous oxalate. The flask and contents were heated to reflux (178° C.) and 19.0 gm of water phase were collected in 10 hours. The excess 2-ethyl-1-butanol and tetrahydronaphthalene were removed on a rotary evaporator to give 474 gm of an oil. The yield was 100%.

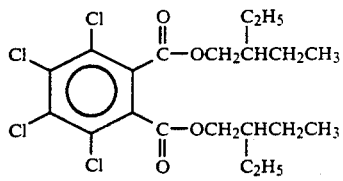

EXAMPLE 44

Into a two liter three-necked flask, euipped with an overhead mechanical stirrer, Dean Stark trap, a water condenser with a nitrogen inlet tube and a thermometer, were charged 463.7 gm (1.0 mol) of tetrabromophthalic anhydride, 408 gm (4.0 mols) of 2-ethyl-1-butanol, 450 gm of tetrahydronaphthalene and 4.64 gm of butylstannoic anhydride. The flask and contents were heated to relux (170° C.) and 20 gm of a water phase were collected in 9 hours. The excess 2-ethyl-1-butanol and tetrahydronapthalene were removed on a rotary evaporator to give 624 gm of a light yellow oil. The yield was 96%.

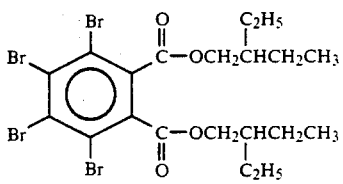

EXAMPLE 45

Into a two liter three-necked flask, equipped with an overhead mechanical stirrer, Dean Stark trap, a water condenser with a nitrogen inlet tube and a thermometer, were charged 285.9 gm (1.0 mol) of tetrachlorophthalic anhydride, 347.5 gm (3.4 mol) of 1-hexanol; 300 gm of tetrahydronapthalene and 3.0 gm of butylstannoic anhydride. The flask and contents were heated to reflux (180° C.) and 18.0 gm of a water phase were collected in 4 hours. The excess 1-hexanol and tetrahydronopthalene were removed on a rotary evaporator to give 466 gm of an oil. The yield was 99%.

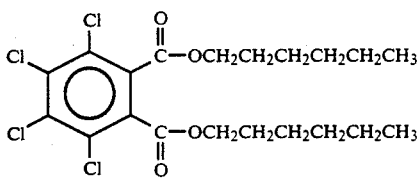

EXAMPLE 46

Into a two liter three-necked flask, equipped with an overhead mechanical stirrer, Dean Stark trap, a water condenser with a nitrogen inlet tube and a thermometer, were charged 463.7 gm (1.0 mol) of tetrabromophthalic anhydride, 347.5 gm (3.4 mol) of 1-hexanol, 300 gm of tetrahydronapthalene and 6.6 gm of butylstannoic anhydride. The flask and contents were heated to reflux (180° C.) and 21.6 gm of a water phase were collected in 6.5 hours. The excess 1-hexanol and tetrahydronaptha-lene were removed on a rotary evaporator to give 623 gm of an oil. The yield was 96%.

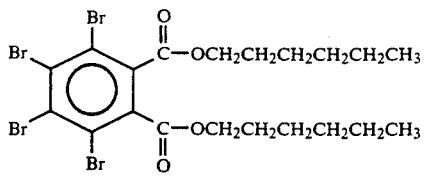

EXAMPLES 47 TO 49 AND COMPARISON EXAMPLE C-1

The following examples and comparison example were prepared to demonstrate the excellent flame retardant characteristic of diesters according to this invention.

A resin blend to be used in examples 47 to 49 and comparison example C-1 was prepared as follows. The following ingredients were mixed, in the indicated order, in a high speed mixer for 5 minutes.

| ingredient | amount in parts by weight (pbw) |
|---|---|
| (a) polyvinyl chloride [sold under the trademark "Geon" by B. F. Goodrich Co., U.S.A.] | 600. |
| (b) dibasic lead phthalate [sold under the trademark "Dythal" by Anzon, Inc., U.S.A.] | 42. |
| (c) clay [sold under the trademark "Satintone" SP 33 by Englehard Corp., U.S.A.] | 60. |
| (d) bisphenol A | 1.8 |
| (e) wax - m.p. 165° F. (about 79° C.) [sold under the trademark "Hostalube" XL165 by Hoechst-Celanese Corp., U.S.A.] | 1.8 |
| (f) antimony oxide | 18.0 |

In each of examples 47 to 49 and in comparison example C-1, 120.6 pbw of the above resin blend were blended with 60 pbw of the ester, and then tested in the following manner. [120.6 pbw of blend is equivalent to 100 pbw of polyvinyl chloride, 7 pbw of dibasic lead phthalate, 10 pbw of clay, 0.3 pbw of bisphenol A, 0.3 pbw of 165° F. wax, and 3 pbw of antimony oxide.] The resin blend and ester were hand stirred for about 1 minute, and then milled into sheets on a two-roll mill at 356° F. (180° C.) for about 4 minutes. The sheets were then compression molded into strips ⅛ in (about 0.32 cm) thick, ¼ in (about 0.64 cm) wide, and 5 in (about 12.7 cm) long, on which the Limited Oxygen Index values were obtained using ASTM (American Society for Testing Materials) Test Procedure D2863-77. The esters tested and the test results are shown in the following table.

| Example | Ester | LOI value |
|---|---|---|
| 47 | di[2-(2-methoxyethoxy)-ethyl] tetrabromophthalate | 56.5 |
| 48 | di[2-(2-ethoxyethoxy)-ethyl-tetrabromophthalate | 53.5 |
| 49 | di(2-butoxyethyl)tetrabromophthalate | 50.5 |
| C-1 | dioctyl phthalate | 28.0 |

As can easily be seen dioctyl phthalate, an alkyl phthalate ester containing neither bromine nor chlorine, known in the art, produced unacceptable flame retardancy. The minimally acceptable LOI value is 40, over 45 being preferred, over 50 most preferred.

We claim:

1. A method for preparing esters of polyhaloaromatic carboxylic acids and anhydrides of the formula:

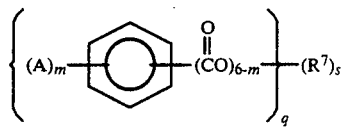

wherein:
(a) the aromatic rings can have all possible isomeric arrangements;
(b) A is Br or Cl;
(c) m is 3, 4, or 5;
(d) q is an integer of 1 to 6;
(e) $R^7$ is
  (i) a substituted or unsubstituted, $C_{1-30}$ alkyl or an aryl having up to 30 carbon atoms, and with a valence (v) which is an integer of 1 to 4;

$$R^3-(OCH_2CH)_p- \atop R^4 \qquad (ii)$$

or $$\begin{array}{cc} R^4 & R^4 \\ | & | \\ -(CHCH_2O)_t CHCH_2- \end{array}$$

where:
$R^3$ is H or a substituted or unsubstituted $C_{1-30}$ alkyl, or an aryl having up to 30 carbon atoms,
$R^4$ is, independently, H or $CH_3$,
p is an integer of 1 to 50, and
t is an integer of 1 to 49; or

 (iii)
$R^5C-$ where $R^5$ is a substituted or unsubstituted, $C_{1-30}$ alkyl or an aryl having up to 30 carbon atoms; and

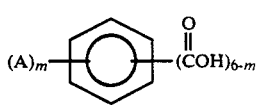 (f)

q, m, and v being as defined above; which comprises reacting:
(I) at least one polyhaloaromatic carboxylic acid or anhydride of the formulae

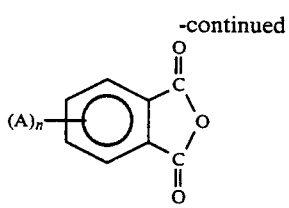 [IIa]

or

-continued

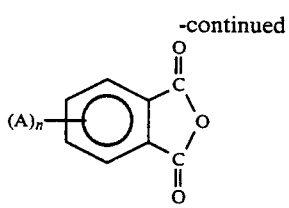 [IIb]

wherein A and m are as defined above and n is 3 or 4; with
(II) at least a stoichiometric quantity of alcohol or polyol of the formula $R^7(OH)_v$ wherein $R^7$ and v are as defined above; and
(III) a catalytically effective amount of Ti-$(OR^2)_4$, wherein $R^2$, independently, is a substituted or unsubstituted $C_{1-30}$ alkyl or a substituted or unsubstituted $C_{2-22}$ alkylene, in the absence of an alkali or alkaline salt.

2. A method according to claim 1 wherein said catalyst is at least one of:
titanium tetraisopropoxide;
titanium tetrabutoxide;
titanium tetra(2-ethyl-1-hexoxide); or
titanium bis(ethyl acetoacetato)diisopropoxy.

3. A method according to claim 1 wherein said polyhaloaromatic carboxylic acid or anhydride is at least one of:

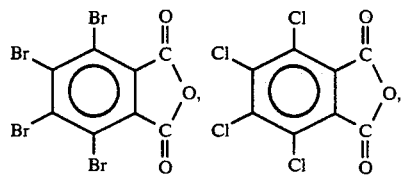

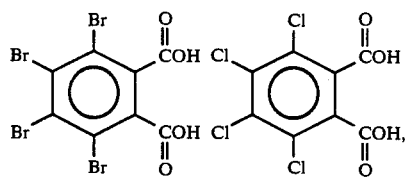

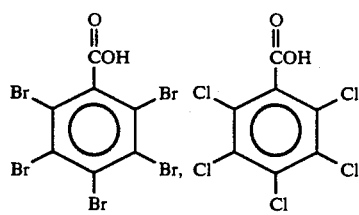

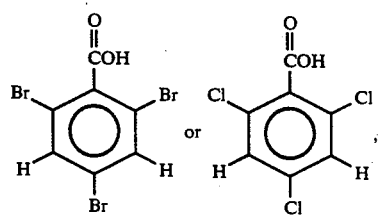

4. A method according to claim 1 wherein said alcohol or polyol is at least one of:

(1) 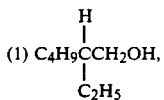 C$_4$H$_9$CCH$_2$OH, (with H above C and C$_2$H$_5$ below)

(2) C$_{12}$H$_{25}$OH,
(3) C$_{18}$H$_{37}$OH,
(4) CH$_3$OCH$_2$CH$_2$OH,
(5) i-C$_9$H$_{19}$OH,
(6) CH$_3$O(CH$_2$CH$_2$O)$_2$H,
(7) C$_4$H$_9$OCH$_2$CH$_2$OH,
(8) HO(CH$_2$CH$_2$O)$_4$H,
(9) i-C$_{10}$H$_{21}$OH,
(10) HO(CH$_2$CH$_2$O)$_6$H,
(11) HO(CH$_2$CH$_2$O)$_{12}$H, or
(12) CH$_3$O(CH$_2$CH$_2$O)$_7$H.

5. A method according to claim 1 wherein said polyhaloaromatic carboxylic acid or anhydride of reactant I is at least one of:
tetrabromophthalic anhydride;
tetrachlorophthalic anhydride;
2,3,5,6-tetraromoterephthalic acid;
2,4,5,6-tetrabromoisophthalic acid; or
tribromophthalic anhydride.

6. A method according to claim 1 wherein said alcohol or polyol of reactant II is at least one of:
2-ethyl-1-hexanol;
1-dodecanol;
1-octanol;
isononyl alcohol;
2-(2-methoxyethoxy)-ethanol;
2-(2-ethoxyethoxy)-ethanol;
isodecyl alcohol;
n-butanol;
1-octadecanol;
cyclohexanol;
1,12-dodecandiol;
1-hexanol;
1-decanol; or
2-ethyl-1-butanol.

* * * * *